US006869802B1

(12) United States Patent
Schwertner et al.

(10) Patent No.: US 6,869,802 B1
(45) Date of Patent: Mar. 22, 2005

(54) COMBINED CHOLESTEROL AND BILIRUBIN TESTS AS RISK PREDICTORS FOR CORONARY ARTERY DISEASE

(75) Inventors: Harvey A. Schwertner, Boerne, TX (US); Joseph R. Fischer, Jr., Boerne, TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 284 days.

(21) Appl. No.: 10/016,825

(22) Filed: Nov. 9, 2001

Related U.S. Application Data

(60) Provisional application No. 60/247,374, filed on Nov. 9, 2000.

(51) Int. Cl.[7] ......................... G01N 33/00; A61K 49/00

(52) U.S. Cl. ............................ 436/71; 424/9.1; 436/97; 436/71

(58) Field of Search ....................... 436/71, 97; 424/9.1

(56) References Cited

U.S. PATENT DOCUMENTS 5,380,667 A * 1/1995 Schwertner .................. 436/71

OTHER PUBLICATIONS

Webster's II Dictionary, New Riverside University Dictionary, 1994, p. 249.*

Kannel et al (Ann. Intern. Med. 90:85–92, 1979).*

* cited by examiner

*Primary Examiner*—Shengjun Wang
*Assistant Examiner*—Shahnam Sharareh
(74) *Attorney, Agent, or Firm*—AFMCLO/JAZ; Fredric L. Sinder

(57) ABSTRACT

A new method for predicting the risk of coronary artery disease (CAD) is disclosed. The method uses a ratio made up of the levels of an individuals LDL-cholesterol (LDL-C), HDL-cholesterol (HDL-C) and serum total bilirubin (bilirubin). The ratio, using a weighted value for bilirubin, is LDL-C/(HDL-C+bilirubin).

2 Claims, 6 Drawing Sheets

CLINICAL AND LABORATORY CHARACTERISTICS OF 644 STUDY SUBJECTS BY DEGREE OF CAD

| | Maximum stenosis | | | |
|---|---|---|---|---|
| CAD RISK FACTORS [a] | 0 - 9% (n = 430) | 10 - 49% (n = 98) | 50 - 100% (n = 116) | P-value |
| Age, years | 39.9 (6.3) | 45.3 (5.9) | 45.3 (5.4) | .000 |
| Cigarettes/day | 5.68 (10.91) | 7.84 (13.57) | 10.59 (13.87) | .000 |
| Systolic blood pressure, mm Hg | 125.7 (13.2) | 126.8 (13.0) | 131.0 (13.3) | .001 |
| Total bilirubin, µmol/L | 14.8 (7.1) | 13.1 (4.7) | 12.5 (5.8) | .001 |
| Total cholesterol, mmol/L | 5.32 (0.99) | 5.91 (0.93) | 6.16 (1.15) | .000 |
| HDL-cholesterol, mmol/L | 1.21 (0.31) | 1.14 (0.26) | 1.11 (0.24) | .002 |
| Triglycerides [b], mmol/L | 1.56 (1.11) | 1.76 (0.92) | 1.87 (0.88) | .009 |
| Cholesterol/HDL-C [c] | 4.71 (1.62) | 5.42 (1.47) | 5.81 (1.59) | .000 |
| (Cholesterol/bilirubin) (÷ 100) [d] | 4.26 (1.91) | 5.11 (1.95) | 5.85 (2.56) | .000 |
| Cholesterol/(HDL-C + bilirubin) [c] | 1.69 (0.59) | 2.01 (0.57) | 2.21 (0.66) | .000 |
| LDL-C/HDL-C [c] | 3.01 (1.11) | 3.64 (1.16) | 3.97 (1.33) | .000 |
| LDL-C/(HDL-C + bilirubin) [c] | 1.08 (0.42) | 1.35 (0.43) | 1.51 (0.53) | .000 |

[a] Values are given as mean ± SD. To convert values for cholesterol, triglycerides, and bilirubin to mg/dL, multiply by 38.66, 88.54, and 0.05847. Analysis of variance. All F-values were significant at P = 0.009.

[b] Triglyceride concentrations are expressed as mmol/L triolein.

[c] Cholesterol/HDL-C, LDL-C/HDL-C, cholesterol/(HDL-C + bilirubin), and LDL-C/(HDL-C + bilirubin) ratios are presented on a mg/dL basis. Bilirubin concentrations were multiplied by 100 before combining with HDL-C. For example, the cholesterol/(HDL-C + bilirubin) ratio was calculated by taking each individual's cholesterol concentration in mg/dL and dividing it by the sum of the HDL-cholesterol concentration in mg/dL plus the bilirubin concentration in mg/dL x 100.

[d] Cholesterol/bilirubin ratios were calculated as the ratio of cholesterol, mmol/L, divided by bilirubin, mmol/L, divided by 100.

CLINICAL AND LABORATORY CHARACTERISTICS OF 644 STUDY SUBJECTS BY DEGREE OF CAD

| | Maximum stenosis | | | |
|---|---|---|---|---|
| **CAD RISK FACTORS** [a] | **0 - 9% (n = 430)** | **10 - 49% (n = 98)** | **50 - 100% (n = 116)** | **P-value** |
| Age, years | 39.9 (6.3) | 45.3 (5.9) | 45.3 (5.4) | .000 |
| Cigarettes/day | 5.68 (10.91) | 7.84 (13.57) | 10.59 (13.87) | .000 |
| Systolic blood pressure, mm Hg | 125.7 (13.2) | 126.8 (13.0) | 131.0 (13.3) | .001 |
| Total bilirubin, μmol/L | 14.8 (7.1) | 13.1 (4.7) | 12.5 (5.8) | .001 |
| Total cholesterol, mmol/L | 5.32 (0.99) | 5.91 (0.93) | 6.16 (1.15) | .000 |
| HDL-cholesterol, mmol/L | 1.21 (0.31) | 1.14 (0.26) | 1.11 (0.24) | .002 |
| Triglycerides [b], mmol/L | 1.56 (1.11) | 1.76 (0.92) | 1.87 (0.88) | .009 |
| Cholesterol/HDL-C [c] | 4.71 (1.62) | 5.42 (1.47) | 5.81 (1.59) | .000 |
| (Cholesterol/bilirubin) (÷ 100) [d] | 4.26 (1.91) | 5.11 (1.95) | 5.85 (2.56) | .000 |
| Cholesterol/(HDL-C + bilirubin) [c] | 1.69 (0.59) | 2.01 (0.57) | 2.21 (0.66) | .000 |
| LDL-C/HDL-C [c] | 3.01 (1.11) | 3.64 (1.16) | 3.97 (1.33) | .000 |
| LDL-C/(HDL-C + bilirubin) [c] | 1.08 (0.42) | 1.35 (0.43) | 1.51 (0.53) | .000 |

[a] Values are given as mean ± SD. To convert values for cholesterol, triglycerides, and bilirubin to mg/dL, multiply by 38.66, 88.54, and 0.05847. Analysis of variance. All F-values were significant at P = 0.009.

[b] Triglyceride concentrations are expressed as mmol/L triolein.

[c] Cholesterol/HDL-C, LDL-C/HDL-C, cholesterol/(HDL-C + bilirubin), and LDL-C/(HDL-C + bilirubin) ratios are presented on a mg/dL basis. Bilirubin concentrations were multiplied by 100 before combining with HDL-C. For example, the cholesterol/(HDL-C + bilirubin) ratio was calculated by taking each individual's cholesterol concentration in mg/dL and dividing it by the sum of the HDL-cholesterol concentration in mg/dL plus the bilirubin concentration in mg/dL x 100.

[d] Cholesterol/bilirubin ratios were calculated as the ratio of cholesterol, mmol/L, divided by bilirubin, mmol/L, divided by 100.

FIG. 1

RESULTS OF DISCRIMINANT ANALYSIS USING TRADITIONAL RISK FACTORS AND VARIOUS LIPID-LIPOPROTEIN AND LIPID-LIPOPROTEIN-BILIRUBIN COMBINATIONS

Discriminant analysis showing variables tested for inclusion into model.

| Variables accepted in model | Wilks' Lambda |
|---|---|
| Age | 0.848 |
| LDL-C/(HDL-C + bilirubin) | 0.839 |
| Systolic blood pressure | 0.769 |
| **Variables not included in model** | |
| Cholesterol/(HDL-C + bilirubin) | 0.757 |
| HDL-cholesterol | 0.757 |
| Triglycerides | 0.757 |
| Cholesterol/HDL-C | 0.755 |
| Cholesterol/bilirubin | 0.755 |
| LDL-C/HDL-C | 0.753 |
| Total bilirubin | 0.751 |
| Cigarettes per day | 0.749 |
| Total cholesterol | 0.749 |

Coronary artery disease classification results.

| | | Predicted Group Membership | | |
|---|---|---|---|---|
| Actual group | No. cases | 0 - 9% | 10 - 49% | 50 - 100% |
| 0 - 9% | 457 | 430<br>94.1% | 3<br>0.7% | 24<br>5.3% |
| 10 - 49% | 98 | 74<br>75.5% | 6<br>6.1% | 18<br>18.4% |
| 50 - 100% | 116 | 74<br>63.8% | 1<br>0.9% | 41<br>35.3% |

FIG. 2

PERCENT CORRECT CLASSIFICATION FOR EACH RISK FACTOR

COMBINATION FOR PREDICTING CORONARY ARTERY DISEASE

Coronary Artery Disease Classification

| Risk Factor Variable | 0 - 9% Specificity % | 10 - 49% | 50 - 100% Sensitivity % | Overall Correct % |
|---|---|---|---|---|
| Age | 97.2 | 0 | 13.8 | 67.4 |
| Age, cholesterol | 95.1 | 4.1 | 23.3 | 68.3 |
| Cholesterol/HDL-C | 97.0 | 0 | 6.8 | 67.2 |
| LDL-C/HDL-C | 97.5 | 0 | 6.9 | 67.6 |
| Cholesterol/bilirubin | 96.8 | 0 | 14.4 | 68.3 |
| Cholesterol/(HDL-C + bilirubin) | 96.1 | 0 | 17.1 | 68.3 |
| LDL-C/(HDL-C + bilirubin) | 96.0 | 0 | 17.9 | 68.4 |
| Laboratory risk factors [b] | 95.1 | 0 | 19.2 | 68.0 |
| Traditional risk factors [c] | 92.8 | 8.2 | 28.4 | 68.3 |
| Traditional and cholesterol/(HDL-C + bilirubin)[d] | 92.1 | 8.2 | 35.3 | 69.1 |
| Traditional and LDL-C/(HDL-C + bilirubin) [e] | 94.1 | 6.1 | 35.3 | 71.1 |

[a] 95% Confidence intervals for sensitivity, specificity, and overall correct are approximately ± 8%, ± 2%, and ± 3%, respectively.
[b] Laboratory risk factors that entered the discriminant model were LDL/(HDL + bilirubin) and cholesterol.
[c] Traditional risk factors examined included cholesterol, cigarettes/day, systolic blood pressure, triglycerides, cholesterol/HDL-C, and HDL-cholesterol. Age, cholesterol, systolic blood pressure, and cigarettes/day entered the discriminant model.
[d] Age, cholesterol/(HDL-C + bilirubin), cholesterol, systolic blood pressure, and cigarettes/day entered the discriminant model.
[e] Age, LDL/(HDL-C + bilirubin), and systolic blood pressure entered the model.

FIG. 3

DIAGNOSTIC PERFORMANCE OF VARIOUS RISK FACTORS FOR PREDICTING SEVERE CORONARY ARTERY DISEASE USING 75TH PERCENTILE AS A CUT-POINT

| Risk Factor Variable [a,c] | Sensitivity (%) | Specificity (%) | Efficiency of Test (%)[b] |
|---|---|---|---|
| Cholesterol/HDL-C | (59/146) 40.4 | (573/731) 78.4 | (632/877) 72.1 |
| LDL-C/HDL-C | (63/145) 43.4 | (577/731) 78.9 | (640/877) 73.0 |
| Cholesterol/bilirubin | (71/146) 48.6 | (584/730) 79.9 | (655/877) 74.7 |
| Cholesterol/(HDL-C + bilirubin) | (76/146) 52.1 | (588/731) 80.4 | (664/877) 75.7 |
| LDL-C/(HDL-C + bilirubin) | (75/145) 51.7 | (587/731) 80.3 | (662/877) 75.5 |

[a] Numbers in parentheses represent the actual subject counts. Cut-points (75th percentile) for the cholesterol/HDL-C ratio, LDL-C/HDL-C ratio, cholesterol/bilirubin ratio, cholesterol/(HDL-C + bilirubin) ratio, and LDL-C/(HDL-C + bilirubin) ratio were 6.04, 4.12, 3.84, 2.25, and 1.5, respectively.
[b] Efficiency of test was calculated as follows: TP + TN/ (TP + TN + FP + FN)
[c] 95% Confidence intervals for sensitivity, specificity, and efficiency of a test are approximately ± 8%, ± 4%, and ± 3%, respectively.

FIG. 4

COMBINED CHOLESTEROL AND BILIRUBIN TESTS AS RISK PREDICTORS FOR CORONARY ARTERY DISEASE

CROSS-REFERENCE TO RELATED APPLICATIONS

This application claims priority under 35 U.S.C. § 119(e) from U.S. provisional application No. 60/247,374, filed Nov. 9, 2000, by Harvey A. Schwertner, Joseph R. Fischer, Jr., Robert Kisselburgh, Ming Wei, Larry W. Gibbons, Qintian Zheng and Steven N. Blair, titled Various Lipid, Lipoprotein and Bilirubin Concentrations as Risk Factors for Predicting Coronary Artery Disease. The invention description contained in that provisional application is incorporated by reference into this description.

This application is related to U.S. application 09/016,826, filed Nov. 9, 2001 by Harvey A. Schwertner and Joseph R. Fisher, Jr., now U.S. Pat. No. 6,720,189, titled Bilirubin Tests as Risk Predictors for Cancer Mortality, Rheumatoid Arthritis, Gilbert's Syndrome and All-Cause Mortality, the invention description of which is incorporated by reference into this application. U.S. Pat. No. 6,720,189 and this application are based on a related series of studies of the utility of bilirubin tests as a risk predictor for various diseases.

RIGHTS OF THE GOVERNMENT

The invention described herein may be manufactured and used by or for the Government of the United States for all governmental purposes without the payment of any royalty.

BACKGROUND OF THE INVENTION

The present invention relates generally to predictive tests for determining the risk of future onset of coronary artery disease, and more particularly to the use of new methods for combining test results for serum total bilirubin with test results for cholesterol to make new ratios as risk predictors for coronary artery disease.

This invention adds to and improves on the teachings of U.S. Pat. No. 5,380,667, issued Jan. 10, 1995, to Harvey A. Schwertner, a co-inventor of the present invention, titled Serum Bilirubin and Liver Function Tests as Risk Predictors for Coronary Artery Disease, the invention description of which is incorporated by reference into this description.

U.S. Pat. No. 5,380,667 showed new non-lipid risk factors for predicting coronary heart disease, most specifically that subacute levels of serum total bilirubin are a significant independent risk predictor for coronary artery disease (CAD). The patent also showed that the ratio of total cholesterol to bilirubin may be used in place of HDL-cholesterol or the ratio of total cholesterol to HDL-cholesterol as a predictor for CAD.

The present invention is the result of additional studies involving bilirubin concentrations and cholesterol levels that provide improved predictive abilities.

There is always a need for improved risk factors for predicting the risk of future coronary artery disease.

It is, therefore, a principal object of the present invention to provide improved coronary risk information.

It is a feature of the present invention that it uses information generally already available from tests already routinely performed.

It is another feature of the present invention that it can be used to diagnose health or the absence of disease.

It is an advantage of the present invention that it improves specificity, sensitivity and accuracy of predictive tests for CAD.

It is another advantage of the present invention that its use will result in fewer false predictions.

It is yet another advantage of the present invention that its use will result in treatment for individuals with CAD to begin at an earlier age.

These and other objects, features and advantages of the present invention will become apparent as the description of certain representative embodiments proceeds.

SUMMARY OF THE INVENTION

The present invention provides a new method for predicting coronary heart disease. The unique discovery of the present invention is that a ratio made up of an individual's LDL-cholesterol (LDL-C), HDL-cholesterol (HDL-C) and serum total bilirubin (bilirubin) more accurately predicts the risk of coronary artery disease than cholesterol levels and ratios alone. The most accurate predictive ratio is LDL-C/(HDL-C+bilirubin).

Accordingly, the present invention is directed to a method characterizing the risk of coronary artery disease for an individual, comprising the steps of obtaining levels of the individual's LDL-cholesterol (LDL-C), HDL-cholesterol (HDL-C) and serum total bilirubin (bilirubin); comparing a ratio of LDL-C/(HDL-C+bilirubin) to a predetermined level for that ratio; and, characterizing from the comparison the risk of coronary artery disease for the individual. The levels making up the ratio may be weighted so that the ratio is a whole number.

DESCRIPTION OF THE DRAWING

The present invention will be more clearly understood from a reading of the following detailed description in conjunction with the accompanying drawings.

FIG. 1 is a table showing the clinical and laboratory characteristics of 644 study subjects by degree of CAD.

FIG. 2 is a table showing the results of discriminant analysis using traditional risk factors and various lipid-lipoprotein and lipid-lipidprotein-bilirubin combinations.

FIG. 3 is a table showing the percent correct classification for each risk factor combination for predicting coronary artery disease.

FIG. 4 is a table showing the diagnostic performance of various risk factors for predicting severe coronary artery disease using $75^{th}$ percentile as a cut-off point.

DETAILED DESCRIPTION

Figure 5:
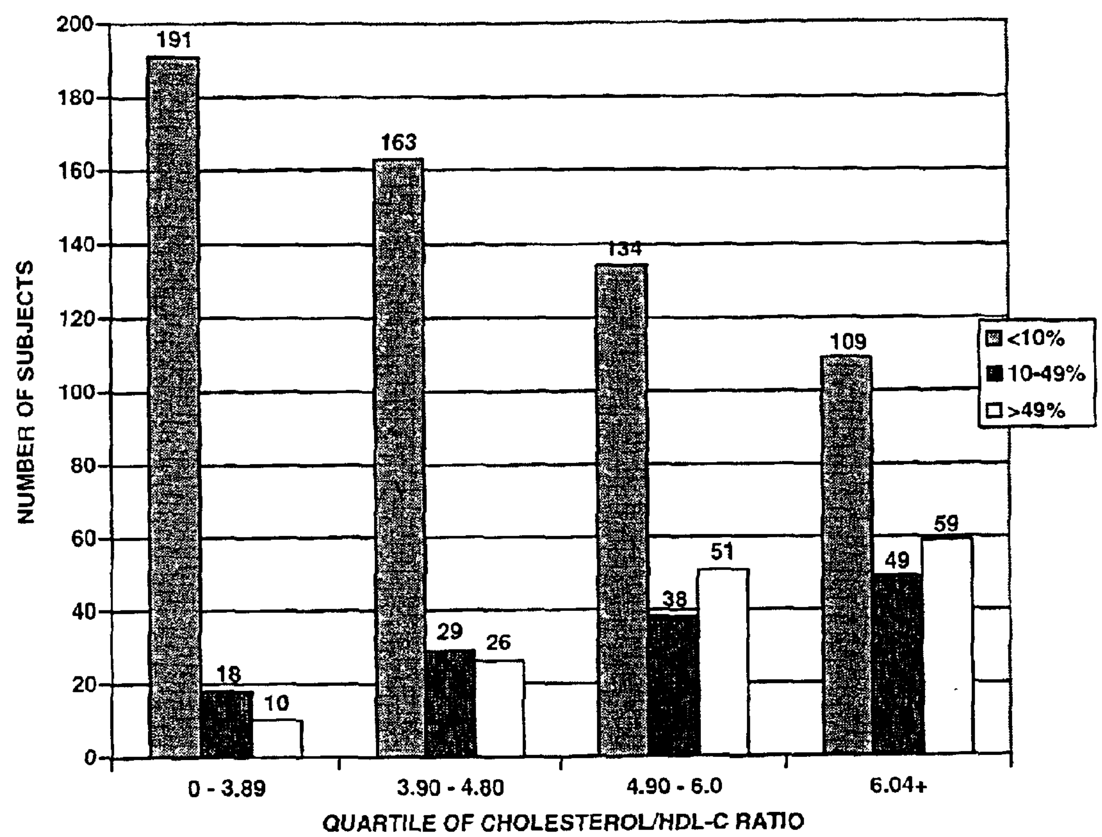
FIGS. 5 and 6 show the prevalence of coronary artery disease in quartile distributions of cholesterol/HDL-cholesterol ratios in FIG. 5 and LDL-C/(HLD-C+bilirubin) ratios in FIG. 6.

Studies were performed to determine if serum bilirubin, when combined with various lipid and lipoprotein risk factors, enhances an ability to predict coronary artery disease (CAD). This hypothesis was tested in a retrospective study of 644 middle-aged males who had undergone coronary angiography. The traditional risk factors of cholesterol, HDL-cholesterol (HDL-C), cholesterol/HDL-C ratios, triglycerides, age, cigarette smoking, and systolic blood pressure were tested by discriminant analysis as were various cholesterol/bilirubin, cholesterol/(HDL-C+bilirubin), and LDL-C/(HDL-C+bilirubin) ratios. Each of these bilirubin-containing ratios was found to be an independent risk predictor when tested with the traditional risk factors. When the LDL-C/(HDL-C+bilirubin) ratio was included with the traditional risk predictors, it improved the prediction of severe CAD from 28.4% to 35.3% and the overall correct classification of CAD from 68.3% to 71.1%. When the 75th percentile was used as a cut-point, the diagnostic sensitivities obtained with cholesterol/(HDL-C+bilirubin) ratios (52.1%) and LDL-C/(HDL-C+bilirubin) ratios (51.7%) were better than those obtained with cholesterol/HDL-C ratios (40.4%) (P=0.033 and 0.048, respectively). LDL-C/(HDL-C+bilirubin) ratios also improved the prediction of severe CAD over those obtained with LDL-C/HDL-C ratios (43.4%), however, the changes were not statistically significant (P=0.096). The teachings of the present invention demonstrates that serum bilirubin may be combined with LDL/HDL-C ratios, cholesterol/HDL-C ratios, cholesterol, or with various apolipoproteins to improve the prediction of CAD.

Introduction

Low serum bilirubin concentrations have been shown to be independently and inversely associated with an increased risk for CAD. The strength of the association between bilirubin and CAD appears to be similar to that of HDL-cholesterol, smoking and systolic blood pressure and CAD. The process by which bilirubin exerts its effect is not known, however, the endogenous antioxidant property of serum bilirubin has been proposed as a possible mechanism. These findings have been recently confirmed in a prospective study of middle-aged British men with ischemic heart disease and in a number of case-control studies involving individuals with coronary artery disease. While these studies have provided important information on serum bilirubin as an independent risk factor for CAD, studies involving an assessment of the accuracy of CAD classification with serum bilirubin have not previously been performed.

Cholesterol, high-density lipoprotein cholesterol (HDL-C) and the cholesterol/HDL-C ratio are often considered to be the major risk factors for coronary artery disease. Of these risk factors, the cholesterol/HDL-cholesterol ratio has been shown to be the most effective discriminator of coronary heart disease. The clinical utility of these risk factors is well established for monitoring purposes and for assessing the risk of cardiovascular disease. The present invention specifically results from a search to determine if the ratio of either total cholesterol/(HDL-cholesterol plus bilirubin) or LDL-cholesterol/(HDL-cholesterol plus bilirubin) is better able to discriminate CAD than either ratio without serum bilirubin. Since both bilirubin and HDL-cholesterol have been shown to be inversely related to CAD, the present invention combines them together in the denominator after adjusting the weight of bilirubin. Such combinations of risk factors permit the use of single values for establishing risk thresholds and for comparing the diagnostic efficiencies at various percentile levels.

The purpose of this cross-sectional study was to assess various serum lipid, lipoprotein, and bilirubin combinations for predicting coronary artery disease in middle-aged men and to compare them to the established lipid and lipoprotein risk factors. For this study, the existing and candidate laboratory risk factors were first compared by themselves to determine which might be most useful for monitoring and screening purposes independent of age, systolic blood pressure, and smoking. A determination was then made to see if the various lipid, lipoprotein, and bilirubin ratios might improve an ability to predict CAD when combined with the established risk factors of age, systolic blood pressure, cigarette smoking, total cholesterol, HDL-cholesterol, cholesterol/HDL-C ratios and triglycerides. A summary of CAD classification results is presented for all of the models studied. In addition, a determination was made of the sensitivities, specificities, and efficiency of a test using the 75th percentile value as a cut-point for the various lipid, lipoprotein, and bilirubin combinations.

Materials And Methods

Subjects

Subjects were 877 asymptomatic male United States Air Force flight crew members who had abnormal exercise tests and who underwent coronary angiography to rule out the presence of CAD. Information on laboratory risk factors were available for all of these subjects, however, complete laboratory and clinical data were available for at least 644 subjects depending on the risk factor being considered. Most subjects were initially identified by subtle serial changes on their routine resting 12-lead electrocardiogram (ECG) obtained during their biennial flight physical. Individuals with serial changes, such as nonspecific ST-T wave changes, underwent a local symptom-limited treadmill test. Those individuals with repolarization or rhythm abnormalities on local stress testing were referred to the USAF Aeromedical Consultation Service at Brooks AFB, Texas.

The cohort used for this study contained 25 additional subjects than the cohort in earlier study that was the basis for U.S. Pat. No. 5,380,667. The subjects were relatively young, physically fit and few were overweight. None had liver disease. Information on medications and vitamin intake was not taken. The frequency of cigarette smoking was taken from the patients' medical records. The data is from individuals who underwent coronary angiography and laboratory testing between 1 Aug. 1978 and 8 May 1990.

Exercise Test Procedures and Coronary Angiography

All individuals underwent a cardiovascular screen which included an ECG at rest, at least 16 hours of ambulatory ECG monitoring, a symptom-limited treadmill test, cardiac fluoroscopy (beginning October 1982), and a thorough history, physical examination and extensive blood tests. The symptom-limited treadmill tests were performed after an overnight fast. The treadmill tests were abnormal if a ST segment depression of 1.0 mm or more occurred 80 ms after the j point. Elective coronary arteriography was performed for abnormal repolarization, decreased thallium uptake, cardiac calcification demonstrated by fluoroscopy, tachycardia, acquired left branch block, or valvular abnormalities. Each angiogram was read jointly by at least two cardiologists. Coronary artery lesions were magnified, traced, and measured with calipers to determine the percentage of diameter narrowing of the artery.

Laboratory Tests

All blood samples were collected after a 12-hour fast and prior to other testing. High-density lipoprotein (HDL) cholesterol was analyzed after precipitation of the apo-B lipoproteins with either phosphotungstate-magnesium reagents or dextran sulfate, Mr, 50,000. Total and HDL-cholesterol were determined enzymatically with BMC Autoflo reagents (Boehringer Mannheim Diagnostics, Indianapolis, Ind.) or with Ciba Corning enzymatic reagents. LDL-cholesterol was calculated by the following formula (10): LDL-C= cholesterol−HDL-C−(triglycerides/5). Total bilirubin was analyzed with diazotized sulfanilic acid reagent with blank correction (Malloy and Evelyn method; Abbott Laboratories and Ciba Corning).

Between-day coefficients of variation (CVs) were 2.5% for the analysis of cholesterol (5.2 mmol/L), 4.6% for HDL-cholesterol (1.3 mmol/L), 5.0% for triglycerides (1.48 mmol/L), and 5.6% for total bilirubin (10.3 $\mu$mol/L). Cholesterol was calibrated against the Abell-Kendall method with cholesterol standards from the National Institute of Standards and Technology (Gaithersburg, Md.). The laboratory participated in both intra- and interlaboratory quality control programs sponsored by the College of American Pathologists.

Statistical Methods

One-way analysis of variance and stepwise discriminant analyses were calculated using SPSS statistical software. McNemar's test (two-tail) was used to determine if bilirubin increases the diagnostic sensitivity of the various lipid and lipoprotein ratios. Coronary artery disease was divided into three groupings according to the maximum coronary stenosis at angiography: 0–9% (no detectable disease), 10%–49% (mild disease), and 50–100% (severe disease). All of the independent variables were treated as continuous variables. Cigarette smoking was measured as the reported average number of cigarettes smoked per day, provided the subject had not quit smoking at least 1 year prior to testing. In all of the total cholesterol or LDL-cholesterol/(HDL-cholesterol plus bilirubin) ratios, the bilirubin concentration was multiplied by 100 and then added to the HDL-cholesterol value before computing the ratios. There was no biological rationale for the weightings of bilirubin. This adjustment was necessary so that bilirubin values would be similar in magnitude to those of HDL-cholesterol. All ratios, except for the cholesterol/bilirubin ratios, were expressed in mg/dL.

Results

Patient Groups and Summary Statistics

Summary statistics are given for groups without CAD, with minimal CAD, and with severe CAD in FIG. 1. In this group of 644, 430 (66.8%) were free of CAD, 98 (15.2%)

had mild CAD, and 116 (18.0%) had severe CAD. All of the clinical and laboratory risk factors were significantly related to severity of CAD. Inverse associations were found for serum total bilirubin and HDL-cholesterol. Summary statistics are not given for the group with 877 individuals. In this group, 597 (68.1%) were free of CAD, 134 (15.3%) had mild disease, and 146 (16.6%) had severe disease.

Discriminant Analysis Models

When the traditional risk factors, age, systolic blood pressure, cigarettes per day, total cholesterol, HDL-cholesterol, cholesterol/HDL-C ratios and triglycerides, were analyzed by discriminant analysis, age, total cholesterol, cigarettes per day and systolic blood pressure were found to be independent risk factors. Cholesterol/HDL-C ratio, HDL-cholesterol and triglycerides did not enter the model once the other four variables were selected. When the traditional risk factors and the various lipid-lipoprotein and lipid-lipoprotein-bilirubin combinations were analyzed by discriminant analysis, age, LDL-C/(HDL-C+bilirubin) ratio and systolic blood pressure were selected for inclusion into the model as shown in FIG. 2.

Summaries of the accuracy of CAD classification for the various risk factors and risk factor combinations analyzed by discriminant analysis either alone or with the traditional risk factors are presented in FIG. 3. When tested individually, the risk factors containing bilirubin were found to be more accurate in classifying severe CAD than either the cholesterol/HDL-C ratios or the LDL-C/HDL-C ratios. The correct classification of severe CAD (diagnostic sensitivity) and the overall correct classification tended to increase in the following order: cholesterol/HDL-C ratio, LDL-C/HDL-C ratio, cholesterol/bilirubin ratio, cholesterol/(HDL-C+bilirubin) ratio, LDL-C/(HDL-C+bilirubin) ratio. HDL-C× bilirubin in the denominator was also multiplied, however, the correct classification was much less than that achieved by adding HDL-C and bilirubin.

When the risk factors containing bilirubin and the traditional risk factors were used to predict CAD, the model containing age, LDL-C/(HDL-C+bilirubin) ratios and systolic blood pressure produced the highest diagnostic sensitivity and the highest percentage of correct results, as shown in FIGS. 2 and 3. Compared to the model containing only the traditional risk factors, the model containing LDL-C/(HDL-C+bilirubin) improved the diagnostic sensitivity for predicting severe CAD from 28.4% to 35.3% and improved the overall correct classification of CAD from 68.3% to 71.1%. The increase in sensitivity was not found to be statistically significant (P=0.15). If the LDL-C/(HDL-C+bilirubin) ratios were omitted from consideration, the cholesterol/(HDL-C+bilirubin) ratios entered the model and produced classification results much like that of LDL-C/(HDL-C+bilirubin) ratios, as shown in FIG. 3.

Discriminant analysis was performed using age and age with cholesterol as variables as shown in FIG. 3. The overall correct classification improved only 0.9% when cholesterol was included with age. The diagnostic sensitivity, however, increased 10.5%.

Classification of CAD Using Quartiles of the Individual Risk Ratios

Figure 6:
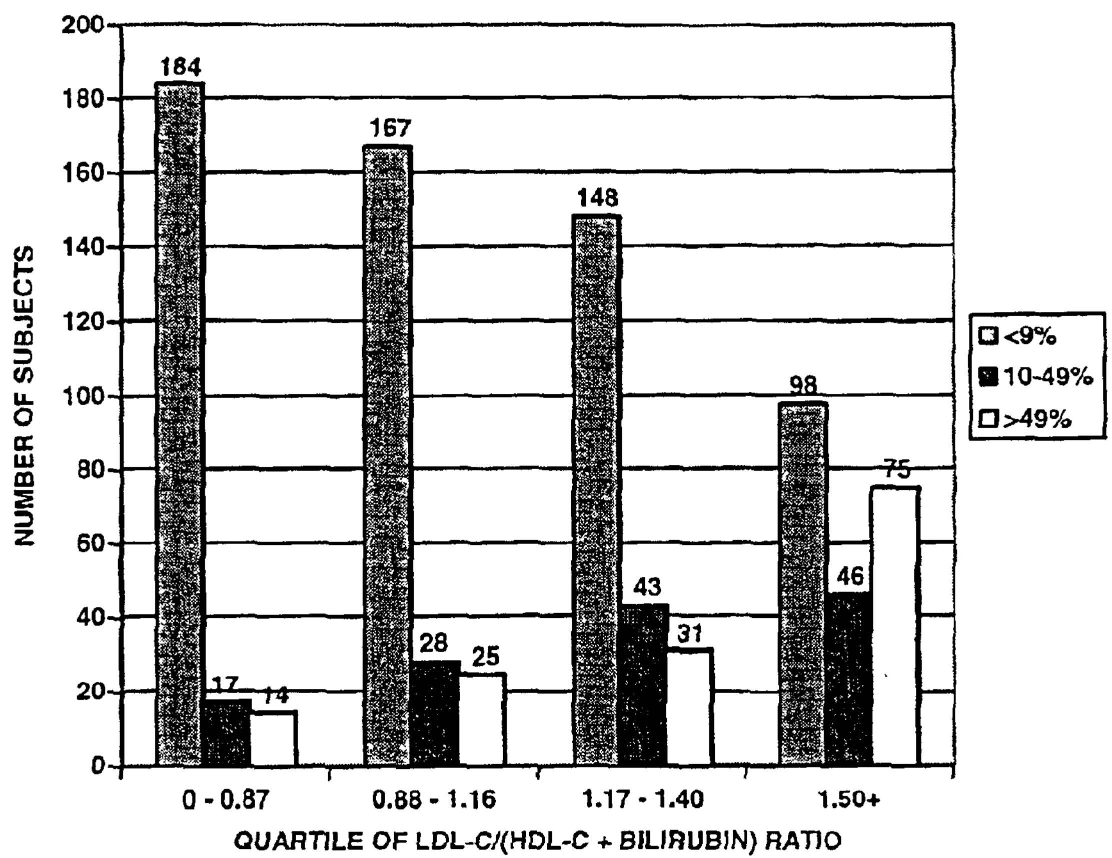

In this approach, the 75th percentile of each risk factor was used as the cut-point to screen for severe CAD. Summaries of diagnostic sensitivities, specificities and the efficiency of a test for predicting severe CAD are presented in FIG. 4. The accuracy of cholesterol/(HDL-C+bilirubin) for predicting severe CAD was found to be similar to that obtained with the LDL-C/(HDL-C+bilirubin) ratios. The diagnostic sensitivities achieved with cholesterol/(HDL-C+bilirubin) and LDL-C/(HDL-C+bilirubin) ratios were higher than those obtained with cholesterol/HDL-C ratios (P=0.033 and 0.048, respectively). The diagnostic sensitivities obtained with LDL-C/(HDL-C+bilirubin) were also better than those obtained with LDL-C/HDL-C ratios, however, the results were not quite significant (P=0.096). As shown in FIGS. 5 and 6, 59 subjects in the fourth quartile were correctly classified as having severe CAD when cholesterol/HDL-C ratios were used to predict CAD compared to 75 when results were based on LDL-C/(HDL-C+bilirubin) ratios.

Discussion

In this study, serum bilirubin was found to increase the predictive value of the major lipid and lipoprotein risk factors. Both the LDL-C/(HDL-C+bilirubin) and the cholesterol/(HDL-C+bilirubin) ratios were found to be more accurate in identifying severe CAD than either the cholesterol/HDL-C or LDL-C/HDL-C ratios. This was found to be true when analyzed by discriminant analysis, or when simply classifying CAD based on quartiles of the predictor variables. In addition, both discriminant analyses and seventy-fifth percentile cut-points produced similar results in ranking the various risk factors.

Numerous studies have been reported on the association between various lipids and lipoproteins and coronary artery disease, however, detailed information on their diagnostic performance have been determined in only a few studies. The present invention shows new risk factor combinations containing bilirubin and how well these risk factors predict CAD. Since serum bilirubin concentrations were previously shown to be inversely related to CAD, positive risk factors were placed in the numerator, e.g., cholesterol and LDL-cholesterol, and negative risk factors, e.g., HDL-cholesterol and bilirubin, in the denominator. The serum bilirubin values were multiplied by 100 so that they would be similar in magnitude to the HDL-cholesterol values. While there is not a specific scientific rationale as to why the ratios seem to work, it is clear that the ratios amplify changes in the numerator, in the denominator, or in both numerator and denominator.

Serum bilirubin increased the overall prediction of CAD approximately 3.0% over that achieved without bilirubin. Even though this increase in predictive ability is not large in absolute terms, none of the traditional risk factors, including cholesterol, produced large increases in overall predictive ability. For example, when an overall prediction was made using age as a variable and then added cholesterol, the overall prediction of CAD increased only 0.9%. The sensitivities, however, increased 10.5% after adding cholesterol. The present invention accurately depicts an ability to predict CAD, while also showing how much further work is needed to accurately predict CAD. Even though a 10 or 20% increase in overall correct classification was hoped for, such increases are difficult to achieve with the current risk factors and risk factor combinations. New risk factors and risk factor combinations will have to be identified to achieve such increases in overall predictive ability.

Further increases in diagnostic accuracy of serum bilirubin can be achieved if the intra- and inter-subject variability in serum bilirubin concentrations can be decreased. The factors that contribute to serum bilirubin variability need to be identified and controlled, if possible, as smaller standard deviations would likely further increase the predictive ability of serum bilirubin. Some of the biological variability of serum bilirubin might be lowered by standardizing the fasting conditions and blood collection times and by using multiple analyses to determine bilirubin concentrations. Even though the variability of serum bilirubin is higher than that of cholesterol, it is similar to that of homocysteine, vitamin C and the lipid soluble vitamins. A smaller portion of the variability is probably analytical in nature and probably results from changes in methods, instruments and manufacturers' calibrators during the 12-year data collection period.

Even though LDL-C/HDL-C+bilirubin ratios were found to be the best predictors of CAD, cholesterol/bilirubin ratios produced results similar to those achieved with cholesterol/HDL-C ratios. In those countries that do not have the resources to analyze HDL-cholesterol, bilirubin should be evaluated as a possible substitute for HDL-cholesterol. Serum bilirubin analysis is simple to perform, reagents and equipment are available in most clinics and hospitals worldwide, and the costs per test are much lower than the costs for analyzing HDL-C. In addition, serum bilirubin appears to be easier to standardize than HDL-cholesterol and reagent and laboratory standardization procedures have already been established to insure accurate quantification of serum bilirubin concentrations. Another advantage for using serum bilirubin is that it appears to be a reflection of the antioxidant status of an individual. Several studies have shown that serum bilirubin is highly correlated with the total antioxidant activity of serum and that bilirubin accounts for 10–30% of the plasma antioxidant activity. Also, the antioxidant capacity of bilirubin has been shown to be higher than that of the lipid soluble vitamins.

Confirmation of these results in women, in other cohorts, and in individuals with diabetes, obesity, or other chronic diseases are needed, but those with skill in the art of the invention will readily see that they are expected. Even though other studies are likely to show some variation in the ranking of the various risk factors containing serum bilirubin, serum bilirubin should increase the predictive value of a given lipid or lipoprotein test.

The present invention shows that serum bilirubin levels when combined with other lipids and lipoproteins can help identify those persons at risk of having arteriosclerosis and those patients who should undergo further testing. Even though the various bilirubin-lipid-lipoprotein risk factors identified have been shown to substantially increase the predictive value of a test, further improvements can be made. In this regard, apolipoprotein B/apolipoprotein A+bilirubin ratios might increase the predictive performance of the apolipoproteins. Homocysteine, fibrinogen, C-reactive protein, oxidized LDL and other independent risk factors, if combined with the lipid-lipoprotein-bilirubin combinations, might increase the ability to predict CAD even further.

This study did not show if bilirubin has a role in preventing CAD. If the association found in this case series is confirmed by other investigations in independent study groups, then studies to elucidate a pathogenic mechanism are needed. Bilirubin is, however, an effective antioxidant, possibly protecting lipids and lipoproteins against oxidation and against plaque formation in humans. Those with skill in the art will see, therefore, that increasing bilirubin may aid in preventing CAD. Similarly, the levels of other antioxidants, such as Vitamins A, C and E, may prove useful as predictors for CAD.

The disclosed new method for predicting the risk of coronary artery disease successfully demonstrates the use of serum bilirubin in combination ratios with cholesterol tests as risk predictors for coronary artery disease. Although the disclosed methods are specialized, their teachings will find application in other areas where careful analysis of existing factors may reveal their suitability as predictive factors for medical diseases, mechanical devices and industrial processes.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

We claim:

1. A method for characterizing the risk of coronary artery disease for an individual, comprising the steps of:

(a) obtaining levels of the individual's LDL-cholesterol (LDL-C), HDL-cholesterol (HDL-C) and serum total bilirubin (bilirubin);

(b) comparing a ratio of LDL-C/(HDL-C+bilirubin) to a predetermined level for that ratio;

(c) characterizing from the comparison the risk of coronary artery disease for the individual;

(d) wherein the HDL-C and bilirubin levels are weighted by multiplying the bilirubin level by 100; and, (e) wherein a ratio above 1.5 characterizes a $75^{th}$ percentile risk of having a coronary stenosis of 50–100% at angiography.

2. A method for characterizing and displaying the risk of coronary artery disease for an individual, comprising the steps of:

(a) obtaining levels of the individual's LDL-cholesterol (LDL-C), HDL-cholesterol (HDL-C) and serum total bilirubin (bilirubin);

(b) comparing a ratio of LDL-C/(HDL-C+bilirubin) to a predetermined level for that ratio;

(c) characterizing from the comparison the risk of coronary artery disease for the individual;

(d) displaying the characterized risk;

(e) wherein the HDL-C and bilirubin levels are weighted by multiplying the bilirubin level by 100; and, (f) wherein a ratio above 1.5 characterizes a $75^{th}$ percentile risk of having a coronary stenosis of 50–100% at angiography.

* * * * *